(12) United States Patent
Mizutani

(10) Patent No.: US 6,911,574 B1
(45) Date of Patent: Jun. 28, 2005

(54) BODY FLUIDS ABSORBENT ARTICLE

(75) Inventor: Satoshi Mizutani, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/487,193

(22) Filed: Jan. 19, 2000

(30) Foreign Application Priority Data

Jan. 19, 1999 (JP) .......................................... 11-011023

(51) Int. Cl.$^7$ ............................................. A61F 13/15
(52) U.S. Cl. .................................... 604/380; 604/383
(58) Field of Search .............................. 604/378, 379, 604/380, 383, 385.01, 385.04

(56) References Cited

U.S. PATENT DOCUMENTS

| | | | |
|---|---|---|---|
| 5,092,860 A | * 3/1992 | Pigneul ...................... | 604/380 |
| 5,382,245 A | * 1/1995 | Thompson et al. ......... | 604/367 |
| 5,383,870 A | 1/1995 | Takai et al. | |
| 5,387,208 A | * 2/1995 | Ashton et al. .............. | 604/358 |
| 5,387,209 A | 2/1995 | Yamamoto et al. | |
| 5,415,640 A | * 5/1995 | Kirby et al. ................ | 604/383 |
| 5,628,844 A | 5/1997 | Nishino et al. | |
| 5,648,142 A | * 7/1997 | Phillips ...................... | 428/132 |

FOREIGN PATENT DOCUMENTS

| | | |
|---|---|---|
| EP | 0 272 683 A2 | 6/1988 |
| EP | 0 781 537 A1 | 7/1997 |
| GB | 2 262 235 A | 6/1993 |
| WO | WO 96/00545 | 1/1996 |
| WO | WO 97/09017 | 3/1997 |

OTHER PUBLICATIONS

Copy of European Search Report mailed Apr. 29, 2002.

* cited by examiner

Primary Examiner—Weilun Lo
Assistant Examiner—Jamisue A Webb
(74) Attorney, Agent, or Firm—Butzel Long

(57) ABSTRACT

A body fluids absorbent article including an absorbent structure that includes a liquid-pervious topsheet, a liquid-impervious backsheet and a liquid-absorbent core disposed therebetween. The topsheet is divided into a first absorbent surface zone and a second absorbent surface zone. The first absorbent surface zone has no gathers and is formed with a plurality of liquid-passages extending therethrough. The second absorbent surface zone is formed with a plurality of gathers extending longitudinally of the absorbent structure. Compressed grooves extend along boundary lines of the first and second absorbent surface zones in transversely opposite side regions of the body facing surface.

12 Claims, 2 Drawing Sheets

BODY FLUIDS ABSORBENT ARTICLE

BACKGROUND OF THE INVENTION

This invention relates to a body fluids absorbent article and more particularly to such an article suitable to be used by women such as a sanitary napkin/pad or pad for incontinent women.

Taking account of the particular purpose for its use, this type article is desired, in general, to have a good characteristic for body fluids such as a high absorptive property as well as a high leakage-proof property. In addition, a comfortable characteristic for the wearer's skin such as a soft touch as well as a breathability is desired because this type article is used in direct contact with the wearer's skin. Obviously, this type article preferably has a combination of these two characteristics. However, it is not easy for the arrangement of prior art to achieve the article satisfying these two characteristics since these two characteristics are partially antinomic to each other. For example, in the case of sanitary napkin, the napkin must be tightly placed against the wearer's skin in order to improve a leakage-proof effect for menstrual discharge. On the other hand, such tight placement causes the napkin to stick to the wearer's skin due to menstrual discharge itself and/or sweat and, in consequence, the wearer may suffer from an uncomfortable feeling, e.g., a sticky and/or stuffy feeling.

It is well known, for example, from Japanese Patent Application Disclosure Gazette (Kokai) No. Hei10-94558 to form the article of the type herein discussed on its body facing surface with a plurality of gathers extending on the central region longitudinally of the body facing surface leaving the lateral regions intact and to form the troughs forming parts of the gathers with a plurality of liquid-passages arranged at regular intervals in the longitudinal direction of the troughs. The invention disclosed in the foregoing document claims that the liquid-passages facilitate the body fluids discharged on the article to be quickly absorbed by the absorbent core and the gathers ensure a good feeling to wear the article by preventing the body facing surface of the article from sticking to the wearer's skin.

However, the lateral regions of the body facing surface are substantially smooth in the article of prior art and at least these lateral regions tend to stick to the wearer's skin due to sweating of the wearer. This may result in an uncomfortable feeling to wear, e.g., a feeling of stickiness. Another important disadvantage lies in the plurality of gathers present in the central region of the body facing surface. These gathers form a plurality of air gaps which affect absorption of menstrual discharge and thereby cause leakage of menstrual discharge. Furthermore, a relatively high rigidity of the gathers is incompatible with delicate body region of the article wearer.

SUMMARY OF THE INVENTION

In view of the problem as has been described above, it is an object of this invention to provide an absorbent article, particularly a sanitary napkin improved to have both characteristics which are antinomic as has been mentioned above. More specifically to describe this, the central region of the body facing surface for which absorption of menstrual discharge is important rather than prevention of an undesirable feeling of stickiness inevitably caused as the body facing surface sticks to the wearer's skin around her vaginal opening due to menstrual discharge and/or sweat of herself should have a high absorptive property. On the other hand, the lateral regions of the body facing surface rather unimportant for absorption of menstrual discharge and having a relatively large area over which these regions are placed against the wearer's skin are effective to prevent the article from sticking to the wearer's skin due to sweating of the wearer.

According to this invention, there is provided a body fluids absorbent article comprising an absorbent structure having a longitudinal center line, a body facing surface and an undergarment facing surface, the absorbent structure comprising a liquid-pervious topsheet defining the skin facing surface, a liquid-impervious backsheet defining the undergarment facing surface and a liquid-absorbent core disposed between the topsheet and the backsheet and the absorbent structure inclusive of the body facing surface being formed in an upper layer thereof with a pair of compressed grooves of arc-shaped cross-sections arranged in bilateral symmetry about the longitudinal center line; wherein:

the topsheet is divided into a first absorbent surface zone extending in a central region thereof and a second absorbent surface zone extending outward from the first absorbent surface zone; the first absorbent surface zone is defined with a substantially smooth surface having no gathers and formed with a plurality of liquid-passages extending therethrough; the second absorbent surface zone is formed with a plurality of gathers extending substantially in parallel to the longitudinal center line; and boundary lines of the first and second absorbent surface zones in transversely opposite facing regions of the body facing surface extend along the pair of compressed grooves.

This invention can additionally include the following features.

Of crests and troughs forming the gathers, each of the crests defines a channel having openings thereof on second boundary lines between the first and second absorbent surface zones in longitudinally opposite end zones of the body side surface.

The topsheet is depressed into and bonded to the absorbent core at least along the pair of compressed grooves.

The pair of compressed grooves describe curves, respectively, convex toward the longitudinal center line.

The liquid-passages have a diameter of 0.3~6 mm, respectively, and are distributed over said first absorbent zone at a throat area ratio of 5~60%.

The liquid-passages are provided in the form of tapered capillaries.

The gathers are 0.3~3 mm high and arranged on said second absorbent surface zone at a pitch of 0.2~5 mm transversely of the second absorbent surface zone.

The first absorbent surface zone extending in the direction of the longitudinal center line and occupies 15~70% of the body facing surface.

The first and second absorbent surface zones are formed by thermoplastic sheets prepared separately of each other and sealed with each other at least along the boundary lines.

The pair of side flaps extend outward from transversely opposite side edges of said core and said side flaps further extend outward in the vicinity of middle regions thereof as viewed in the direction of the longitudinal center line to define a pair of wings.

DETAILED DESCRIPTION OF THE PREFERRED EMBODIMENTS

Details of this invention will be more fully understood from the description of a sanitary napkin as a specific embodiment of an absorbent article according to this invention given hereunder with reference to the accompanying drawings.

Figure 1:
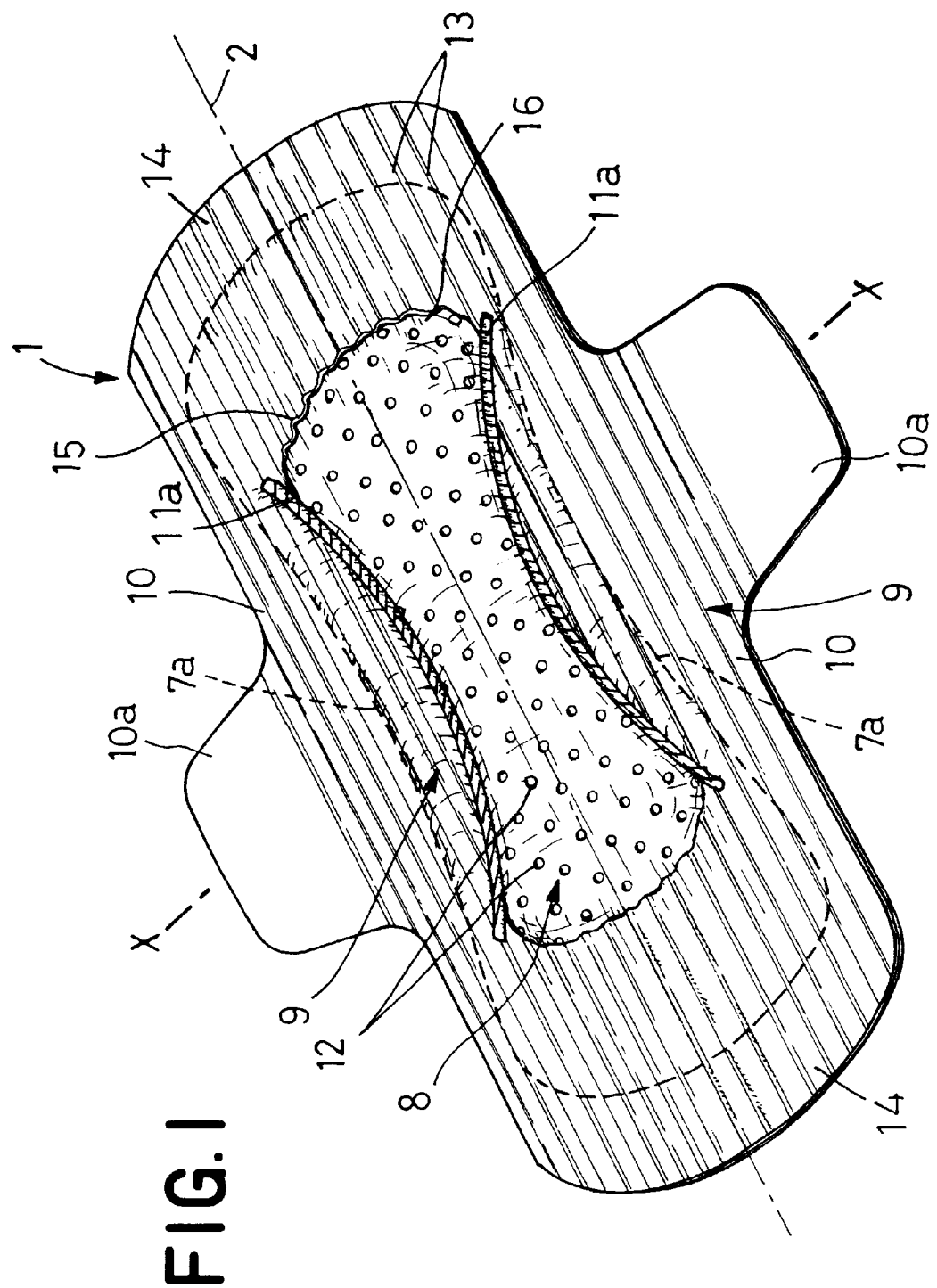
FIG. 1 is a perspective view showing a sanitary napkin as a specific embodiment of the absorbent article according to this invention.
Figure 2:
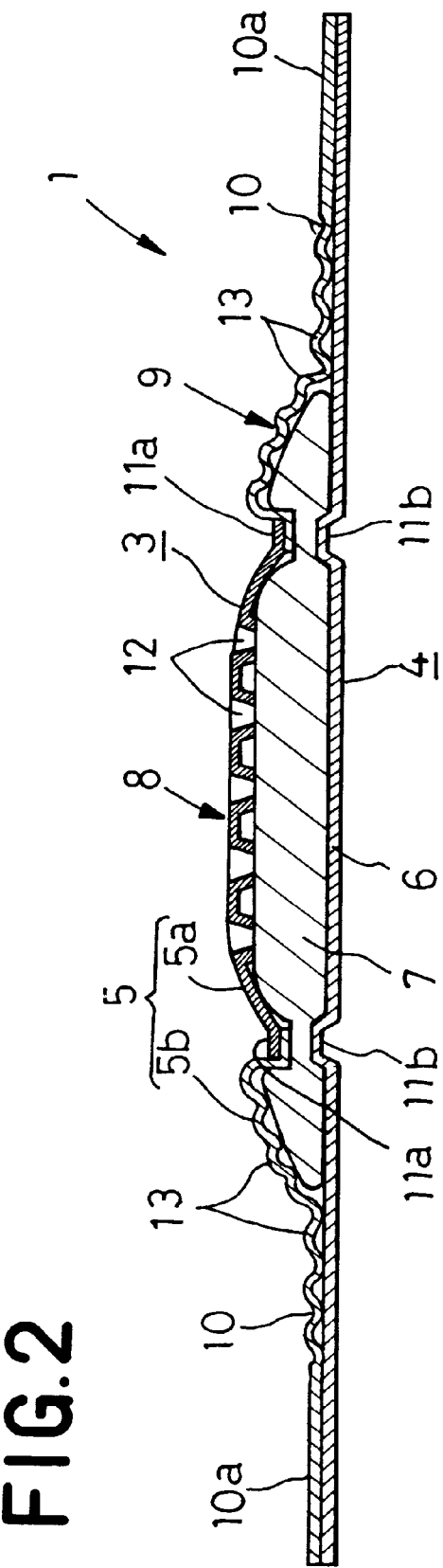
FIG. 2 is a scale-enlarged schematic sectional view taken along a line X—X in FIG. 1.

Referring to FIGS. 1 and 2, a sanitary napkin includes an absorbent structure symmetrically shaped about a center line 2 extending longitudinally thereof and having a body facing surface (upper surface as viewed in FIGS. 1 and 2) 3 and undergarment facing surface (lower surface as viewed in FIGS. 1 and 2) 4. The absorbent structure 1 comprises a liquid-pervious topsheet 5 defining the body facing surface 3, a liquid-impervious backsheet 6 defining the undergarment facing surface 4 and a liquid-absorbent core 7 disposed between these two sheets 5, 6 and being thicker than them.

The topsheet 5 has a high flexibility and comprises a thermoplastic sheet 5a forming a first absorbent surface zone 8 extending over a central region of the body facing surface and a thermoplastic sheet 5b forming a second absorbent surface zone 9 extending outward from the first absorbent surface zone 8. The backsheet 6 also has a high flexibility and forms the entire rear surface of the absorbent structure 1. The absorbent core 7 is semi-rigid but has an appropriate compressive stability. Transversely opposite side edges 7a of the absorbent core 7 describe a pair of curves which are convex toward the longitudinal center line 2.

A section (sheet 5b) of the topsheet 5 extending outward beyond a peripheral edge of the absorbent core 7 is put flat together with a section of the backsheet 6 also extending outward beyond the peripheral edge of the absorbent core 7 to form a pair of side flaps 10, 10, a pair of end flaps 14, 14 and a pair of wings 10a, 10a. Each of the wings 10a, 10a. extends outward from the associated side flap 10 in the vicinity of its middle zone so that the wing 10a. is opposed to the associated with the curved side edge 7a of the absorbent core 7 in alignment with the longitudinally middle section of the curved side edge 7a. Such relative position of the curved side edge 7a, 7a of the absorbent core 7 and the wings 10a, 10a. facilitates the napkin to be fastened to an undergarment worn by a wearer. Specifically, the side flaps 10, 10 can be easily folded along their transversely middle zones substantially over their full length back onto the lower surface of the undergarment's crotch region without generation of undesired creases not only along the curved side edges 7a, 7a of the absorbent core 7 but also along curved side edges of the undergarment.

The absorbent structure 1 formed with pairs of compressed grooves 11a, 11a; 11b, 11b on its upper and lower surfaces, respectively, which are symmetric about the longitudinal center line 2 and extend across transversely opposite lateral zones of the absorbent core 7 to describe convex curves toward the longitudinal center line 2. These compressed grooves 11a, 11a; 11b, 11b are formed by depressing the topsheet 5 and the backsheet 6 and both surfaces of the absorbent core 7. When the napkin is put on the body, these compressed grooves 11a, 11a; 11b, 11b function as folding lines along which the second absorbent surface zone 9 extending outside the compressed grooves 11a, 11a; 11b, 11b can be bent relative to the first absorbent surface zone 8. A curvature defining these compressed grooves 11a, 11a; 11b, 11b is such that the portion of the absorbent core 7 lying in the second absorbent surface zone 9 may be smoothly bent and fit the curved surfaces of the wearer's thighs. It should be understood that the pair of compressed grooves 11b, 11b may be eliminated. Even when the lower surface of the absorbent core 7 is formed with the pair of compressed grooves 11b, 11b, the manner in which they are implemented is not limited to that as illustrated. For example, the absence of the compressed grooves 11b, 11b on the lower surface of the absorbent core 7 may be the pair of correspondingly deeper compressed grooves 11a, 11a on the upper surface of the absorbent core 7.

The absorbent structure 1, particularly the first absorbent surface zone 8 has a cross-section progressively slopes down from its transverse middle toward its transversely opposite side edges. The surface of the first absorbent surface zone 8 is substantially smooth and effective to prevent menstrual discharge from flowing between the first absorbent surface zone 8 and the wearer' skin by closely fitting a concave region defined between the large pudendal lips of the wearer. The first absorbent surface zone 8 extends in parallel to the longitudinal center line 2 to occupy 15~70% of the entire body side surface of the absorbent structure 1 and has a plurality of liquid passages 12 extending through the first absorbent surface zone 8. In order to ensure that menstrual discharge can be efficiently guided through the liquid passages 12 and absorbed by the absorbent core 7, each of the liquid passages 12 is preferably provided in the form of a tapered capillary having a diameter of 0.3~6 mm at its top with a total throat area ratio being in a range of 5~60% in the first absorbent surface zone 8.

The second absorbent surface zone 9 has a plurality of gathers 13 extending substantially in parallel to the longitudinal center line 2. The gathers 13 are preferably provided to be distributed at a pitch of 0.2~5 mm transversely of the respective second absorbent surface zone 9 and to have a height of 0.3~3 mm in order to ensure functions such as appropriate breathability and restoring elasticity against compression between the second absorbent surface zone 9 and the wearer's skin. Of crests and troughs forming the gathers 13, each crest is preferably formed so as to define a continuous channel in order to improve the breathability and restoring elasticity against compression. The channels of the gathers 13 open along a border 15 between the first absorbent surface zone 8 and the second absorbent surface zone 9 in the vicinity of longitudinally opposite end areas on the body facing surface 3. Menstrual discharge partially flows from the first absorbent surface zone 8 into openings 16 of the respective channels before absorbed by the absorbent core 7. Correspondingly, a possibility that the longitudinally opposed end areas of the second absorbent surface zone 9 could be soiled with menstrual discharge is alleviated. Of the crests and the troughs forming the gathers 13, each trough may be formed at regular intervals longitudinally thereof with second liquid passages (not shown), whereby an amount of menstrual discharge flowing into the second absorbent surface zone 9 may rapidly transferred to the absorbent core 7 and the breathability may be further improved. The gathers 13 can be easily obtained, for example, by feeding a thermoplastic nonwoven fabric between a pair of heated rolls having grooves and ridges on their peripheral surfaces.

The thermoplastic sheet 5a forming the first absorbent surface zone 8 and the thermoplastic sheet 5b forming the second absorbent surface zone 9 are sealed with each other at least along the compressed grooves 11a, 11a. While the portions of the thermoplastic sheets 5a, 5b sealed with each other in this manner are necessarily of high rigidity and would otherwise irritate the wearer's skin, the compressed grooves 11a, 11a effectively protect the wearer's skin from being in direct contact with the rigid portions and irritate thereby. Generally, a thermoplastic film or thermoplastic nonwoven fabric is useful as stock material for the thermoplastic sheets 5a, 5b. Particularly in the illustrated embodiment of this invention, at least two different types of stock material may be used in a combination depending on the characteristics expected for the napkin, taking account of its unique arrangement such that the absorbent surface is divided in the first and second absorbent surface zones 8, 9. For example, the first absorbent surface zone 8 may be formed by a thermoplastic film and the second absorbent surface zone 9 may be formed by a thermoplastic nonwoven fabric. It is also possible to arrange so that the first absorbent surface zone 8 has a degree of hydrophilicity or hydrophobicity different from that of the second absorbent surface zone 9, for example, the former has a degree of hydrophilicity higher than that of the latter. Obviously, it is possible to use a thermoplastic nonwoven fabric as stock material for both the first and second absorbent surface zones 8, 9. In general, component fibers of the thermoplastic nonwoven fabric useful for this purpose may be selected from a wide range including polyolefine, polyester and polyamide fibers, and polyethylene/polypropylene or polyester conjugated fibers, each of 1~8 deniers. In order that a possibility of menstrual discharge staying on the absorbent surface can be alleviated and a tear strength of the absorbent surface can be improved, a fineness is preferably adjusted to be in a range of 1.5~6.0 deniers. The thermoplastic nonwoven fabric useful for this purpose may take various forms such as spun lace, needle punch, melt blown, thermal bond, spun bond and chemical bond nonwoven fabrics. A basis weight of such nonwoven fabrics are preferably in a range of 15~80 g/m$^2$ and more preferably in a range of 20~60 g/m$^2$ to assist the formation of the gathers 13.

In the peripheral region of the absorbent structure 1, the topsheet 5 and the backsheet 6 are bonded to each other utilizing bonding means of well known art such as hot melt adhesive or heat-sealing technique. When the hot melt adhesive is utilized, it is important in the regions of the side flaps 10, 10, particularly in the outer regions of the side flaps including the respective wings 10a, 10a to distribute the hot melt adhesive (not shown) between the topsheet 5 and the backsheet 6 as evenly as possible and thereby to improve a tear strength of the side flaps. This is for the reason that at least the wings 10a, 10a. must have a desired tear strength. More specifically, the wings 10a, 10a. are destined to be pulled outward and downward so as to wrap the crotch region of the undergarment and to be adhesively fastened to the lower surface of the crotch region. After use of the napkin, the wings 10a, 10a. are destined to be forcibly peeled off from the crotch region of the undergarment. Use of the hot melt adhesive in this manner is particularly suitable for the case in which the backsheet 6 comprises a polyolefine film (particularly polyethylene film) having a thickness less than 100 µ and a moisture-permeable property. Such film is usually made moisture-permeable by addition of filler in the form of fine grains and by subjecting the film to a process of drawing. Consequently, such film inevitably has a plurality of cleavages and its tear strength is lower than that of moisture-impermeable film. Evenly distribution of the hot melt adhesive is effective to compensate such poor tear strength.

The backsheet 6 may be formed by a thermoplastic film, a fibrous sheet being relatively high in a liquid-resistance as well as in a strength, for example, a conjugated nonwoven fabric consisting of a melt blown fiber nonwoven fabric and a spun bond nonwoven fabric laminated on the outer surface thereof. The absorbent core 7 may be formed substantially by a mixture of fluff pulp and superabsorptive hydrogel particles in the form of a panel or a mat, which is entirely wrapped with a water-absorbent sheet such as tissue paper.

It is possible to dispose a fibrous layer (not shown) having a relatively low fiber density and a good cushioning property at least between the topsheet 5 and the core 7. This fibrous layer ensures the topsheet 5 to be sufficiently spaced from the upper surface of the absorbent core 7 to prevent menstrual discharge from flow back toward and exuding through the upper surface of the topsheet 5. In addition, the fibrous layer is remarkably effective to improve, in the upper layer of the absorbent structure 1, a restoring elasticity from compression and thereby to give the wearer a feeling of softness.

While the sanitary napkin has been described hereinabove, this invention is applicable to the other body fluids absorbent articles such as a pad for incontinent women. Furthermore, it will be understood by those skilled in the art that various additional embodiments may be contemplated without departing from the spirit and scope of this invention.

The unique arrangement according to this invention makes the body fluids absorbent article, particularly such article for women very suitable for practical use. As will be apparent from the foregoing description, the first absorbent surface zone which is most important for absorption of body fluids such as menstrual discharge closely fits a vaginal opening of the wearer to restrict a free flow of the body fluids and thereby to achieve an efficient absorption of the body fluids. On the other hand, the second absorbent surface zone is not important for absorption of the body fluids but adapted to come in contact with the wearer's skin over a relatively large area. This second absorbent surface zone serves to improve a breathability and effectively prevents this second absorbent surface zone from sticking to the wearer's skin due to sweating. In this way, the problems left behind unsolved by the prior art can be effectively solved.

The body facing surface of the absorbent article divided into the first and second absorbent surfaces allows these two absorbent surface zones to be formed by different stock materials depending on the particular characteristics expected for these two absorbent surface zones. To form these two absorbent surface zones by two different stock materials, respectively, they must be bonded to each other by some means. In this case, there would otherwise occur any apprehension that the bonded region along which these two stock materials are bonded to each other might irritate the wearer's skin. However, this invention effectively eliminates such apprehension by the compressed grooves extending along the bonded region and functioning to space the bonded region from the wearer's skin. In this manner, the body facing surface of the absorbent article is reliably free from any apprehensive skin irritation in spite of the presence of the bonded region.

What is claimed is:

1. A body fluids absorbent article comprising:
    an absorbent structure having a longitudinal center line;
    a body facing surface; and
    an undergarment facing surface,
    said absorbent structure comprising:
        a liquid-pervious topsheet defining said body facing surface;
        a liquid-impervious backsheet defining said undergarment facing surface; and a liquid-absorbent core disposed between said topsheet and said backsheet, said absorbent structure inclusive of said body facing surface being formed in an upper layer thereof with a pair of compressed grooves, each of said compressed grooves having opposite terminal ends and a length extending between and to the opposite terminal ends, said compressed grooves being curved along the entire lengths thereof and being arranged in bilateral symmetry about said longitudinal center line, and extending continuously between longitudinal opposite ends of said absorbent structure, said topsheet being divided into a first absorbent surface zone extending in a central regions thereof and a second absorbent surface zone extending outward from said first absorbent surface zone, said first absorbent surface zone having a substantially smooth surface having no gathers and formed with a plurality of liquid-passages extending therethrough, said second absorbent surface zone having a plurality of gathers that extend substantially in parallel to said longitudinal center line, said first and second absorbent surface zones having boundary lines in transversely opposite side regions of said body facing surfaces that extend along said pair of compressed grooves.

2. The article according to claim 1, wherein, of crests and troughs forming said gathers, each of said crests defines a channel having openings thereof on second boundary lines between said first and second absorbent surface zones in longitudinally opposite end zones of said body facing surface.

3. The article according to claim 1, wherein said topsheet is depressed into and bonded to said absorbent core at least along said pair of compressed grooves.

4. The article according to claim 1, wherein said pair of compressed grooves describe curves, respectively, convex toward said longitudinal center line.

5. The article according to claim 1, wherein said first absorbent zone is positioned in a central zone of both longitudinal and transverse directions of said article.

6. The article according to claim 1, wherein said liquid-passages are provided in the form of tapered capillaries.

7. The article according to claim 1, wherein said plurality of gathers are about 0.3 to about 3 mm high and arranged on said second absorbent surface zone at a pitch of about 0.2 to about 5 mm transversely of said second absorbent surface zone.

8. The article according to claim 1, wherein said first absorbent surface zone extends in the direction of said longitudinal center line and occupies about 15 to about 70% of said body facing surface.

9. The article according to claim 1, wherein said first and second absorbent surface zones are formed by thermoplastic sheets prepared separately of each other and sealed with each other at least along said boundary lines.

10. The article according to claim 1, wherein a pair of side flaps extend outward from transversely opposite side edges of said absorbent core and said side flaps further extend outward in the vicinity of middle regions thereof as viewed in the direction of said longitudinal center line to define a pair of wings.

11. The article according to claim 1, wherein said liquid-passages have diameters of about 0.3 to about 6 mm.

12. The article according to claim 5, wherein said liquid-passages are distributed over said first absorbent zone at a throat area ratio of about 5 to about 60%.

* * * * *